United States Patent
Fein et al.

(10) Patent No.: US 8,639,307 B2
(45) Date of Patent: *Jan. 28, 2014

(54) OXIMETER SENSOR WITH DIGITAL MEMORY ENCODING SENSOR DATA

(75) Inventors: Michael E. Fein, Mountain View, CA (US); Marcia Fein, legal representative, Mountain View, CA (US); Paul D. Mannheimer, Danville, CA (US); Adnan Merchant, Fremont, CA (US); Charles Porges, Orinda, CA (US); David Swedlow, Danville, CA (US)

(73) Assignee: Covidien LP, Mansfield, MA (US)

( * ) Notice: Subject to any disclaimer, the term of this patent is extended or adjusted under 35 U.S.C. 154(b) by 1718 days.

This patent is subject to a terminal disclaimer.

(21) Appl. No.: 11/445,126

(22) Filed: Jun. 1, 2006

(65) Prior Publication Data

US 2006/0229511 A1    Oct. 12, 2006

Related U.S. Application Data

(63) Continuation of application No. 10/440,560, filed on May 16, 2003, now Pat. No. 7,085,597, which is a continuation of application No. 09/943,805, filed on Aug. 30, 2001, now Pat. No. 6,591,123.

(60) Provisional application No. 60/229,616, filed on Aug. 31, 2000.

(51) Int. Cl.
*A61B 5/1455*    (2006.01)

(52) U.S. Cl.
USPC ............................................. 600/323

(58) Field of Classification Search
USPC .......................................... 600/323, 310, 322
See application file for complete search history.

(56) References Cited

U.S. PATENT DOCUMENTS

| | | |
|---|---|---|
| 3,720,199 A | 3/1973 | Rishton et al. |
| 3,790,910 A | 2/1974 | McCormack |
| 3,797,479 A | 3/1974 | Graham |
| 4,041,935 A | 8/1977 | Garbe |
| 4,210,155 A | 7/1980 | Grimes |
| 4,303,984 A | 12/1981 | Houvig |
| 4,446,715 A | 5/1984 | Bailey |
| 4,621,643 A | 11/1986 | New, Jr. et al. |
| 4,653,498 A | 3/1987 | New, Jr. et al. |
| 4,684,245 A | 8/1987 | Goldring |
| 4,684,246 A | 8/1987 | Downing |
| 4,700,708 A | 10/1987 | New, Jr. et al. |
| 4,714,080 A | 12/1987 | Edgar et al. |
| 4,717,080 A | 1/1988 | Sauer |
| 4,734,873 A | 3/1988 | Malloy et al. |

(Continued)

FOREIGN PATENT DOCUMENTS

| | | |
|---|---|---|
| DE | 3028061 | 9/1982 |
| EP | 0 949 506 A2 | 10/1999 |

(Continued)

*Primary Examiner* — Eric Winakur

(57) ABSTRACT

Embodiments of the present invention include systems and methods that relate to a sensor with memory. Specifically, one embodiment includes a method of sensor operation, comprising emitting light from a light emitting element of the sensor, detecting the light with a light detecting element of the sensor, storing sensor model identification data within a memory of the sensor, and providing access to the memory to facilitate reading the sensor model identification data with an oximeter monitor.

11 Claims, 1 Drawing Sheet

(56) References Cited

U.S. PATENT DOCUMENTS

| | | |
|---|---|---|
| 4,845,649 A | 7/1989 | Eckardt et al. |
| 4,845,873 A | 7/1989 | Hazlett |
| 4,858,615 A | 8/1989 | Meinema |
| 4,862,872 A | 9/1989 | Yabe et al. |
| 4,868,476 A | 9/1989 | Respaut |
| 4,913,150 A | 4/1990 | Cheung |
| 4,942,877 A | 7/1990 | Sakai et al. |
| 5,007,423 A | 4/1991 | Branstetter |
| 5,008,843 A | 4/1991 | Poelsler et al. |
| 5,016,198 A | 5/1991 | Schreiber |
| 5,025,374 A | 6/1991 | Roizen et al. |
| 5,025,791 A | 6/1991 | Niwa |
| 5,058,588 A | 10/1991 | Kaestle |
| 5,070,732 A | 12/1991 | Duncan et al. |
| 5,162,725 A | 11/1992 | Hodson et al. |
| 5,226,417 A | 7/1993 | Swedlow et al. |
| 5,233,520 A | 8/1993 | Kretsch et al. |
| 5,246,003 A | 9/1993 | DeLonzor |
| 5,259,381 A | 11/1993 | Cheung et al. |
| 5,329,931 A | 7/1994 | Clauson et al. |
| 5,341,291 A | 8/1994 | Roizen et al. |
| 5,347,476 A | 9/1994 | McBean, Sr. |
| 5,360,005 A | 11/1994 | Wilk |
| 5,365,462 A | 11/1994 | McBean, Sr. |
| 5,368,026 A | 11/1994 | Swedlow et al. |
| 5,371,128 A | 12/1994 | Ulman et al. |
| 5,372,141 A | 12/1994 | Gallup et al. |
| 5,385,144 A | 1/1995 | Yamanishi et al. |
| 5,425,375 A | 6/1995 | Chin |
| 5,429,129 A | 7/1995 | Lovejoy et al. |
| 5,431,170 A | 7/1995 | Mathews |
| 5,443,801 A | 8/1995 | Langford |
| 5,448,991 A | 9/1995 | Polson et al. |
| 5,471,382 A | 11/1995 | Tallman et al. |
| 5,513,646 A | 5/1996 | Lehrman et al. |
| 5,528,519 A | 6/1996 | Ohkura et al. |
| 5,627,531 A | 5/1997 | Posso et al. |
| 5,645,059 A | 7/1997 | Fein et al. |
| 5,645,060 A | 7/1997 | Yorkey |
| 5,645,069 A | 7/1997 | Lee |
| 5,660,163 A | 8/1997 | Schulman et al. |
| 5,660,176 A | 8/1997 | Iliff |
| 5,678,448 A | 10/1997 | Fullen et al. |
| 5,682,877 A | 11/1997 | Mondry |
| 5,718,235 A | 2/1998 | Golosarsky et al. |
| 5,720,293 A | 2/1998 | Quinn et al. |
| 5,730,124 A | 3/1998 | Yamauchi |
| 5,758,644 A | 6/1998 | Diab |
| 5,800,350 A | 9/1998 | Coppleson et al. |
| 5,818,583 A | 10/1998 | Sevick-Muraca et al. |
| 5,830,121 A | 11/1998 | Enomoto et al. |
| 5,830,135 A | 11/1998 | Bosque |
| 5,855,609 A | 1/1999 | Knapp |
| 5,865,736 A | 2/1999 | Baker, Jr. et al. |
| 5,954,644 A | 9/1999 | Dettling et al. |
| 5,961,446 A | 10/1999 | Beller |
| 5,964,701 A | 10/1999 | Asada et al. |
| 5,987,343 A | 11/1999 | Kinast |
| 5,995,859 A | 11/1999 | Takahashi |
| 6,004,276 A | 12/1999 | Wright et al. |
| 6,018,673 A | 1/2000 | Chin et al. |
| 6,023,541 A | 2/2000 | Merchant et al. |
| 6,044,283 A | 3/2000 | Fein et al. |
| 6,095,984 A | 8/2000 | Amano et al. |
| 6,104,938 A | 8/2000 | Huiku et al. |
| 6,122,536 A | 9/2000 | Sun et al. |
| 6,241,679 B1 | 6/2001 | Curran |
| 6,298,252 B1 * | 10/2001 | Kovach et al. ............... 600/331 |
| 6,298,255 B1 | 10/2001 | Cordero |
| 6,308,089 B1 | 10/2001 | von der Ruhr et al. |
| 6,356,774 B1 | 3/2002 | Bernstein et al. |
| 6,360,114 B1 | 3/2002 | Diab et al. |
| 6,374,129 B1 | 4/2002 | Chin et al. |
| 6,377,829 B1 | 4/2002 | Al-Ali |
| 6,405,087 B1 | 6/2002 | Snell |
| 6,463,310 B1 | 10/2002 | Swedlow et al. |
| 6,466,808 B1 | 10/2002 | Chin |
| 6,591,123 B2 | 7/2003 | Fein |
| 6,608,934 B2 | 8/2003 | Scheirer et al. |
| 6,708,049 B1 | 3/2004 | Berson et al. |
| 6,801,797 B2 | 10/2004 | Mannheimer et al. |
| 6,845,256 B2 | 1/2005 | Chin et al. |
| 6,934,571 B2 | 8/2005 | Wiesmann et al. |
| 6,950,687 B2 | 9/2005 | Al-Ali |
| 6,979,812 B2 | 12/2005 | Al-Ali |
| 6,988,056 B2 | 1/2006 | Cook |
| 7,048,687 B1 | 5/2006 | Reuss et al. |
| 7,187,441 B1 | 3/2007 | Sevick-Muraca et al. |
| 7,260,425 B2 | 8/2007 | Chin et al. |
| 7,272,425 B2 | 9/2007 | Al-Ali |
| 7,457,652 B2 | 11/2008 | Porges et al. |
| 2002/0103423 A1 | 8/2002 | Chin et al. |
| 2003/0135099 A1 | 7/2003 | Al-Ali |
| 2005/0070773 A1 | 3/2005 | Chin et al. |
| 2005/0070775 A1 | 3/2005 | Chin et al. |
| 2005/0165323 A1 | 7/2005 | Montgomery et al. |
| 2006/0030763 A1 | 2/2006 | Mannheimer et al. |
| 2006/0030764 A1 | 2/2006 | Porges et al. |
| 2006/0161054 A1 | 7/2006 | Reuss et al. |
| 2006/0224059 A1 | 10/2006 | Swedlow et al. |
| 2006/0259925 A1 | 11/2006 | Lemmons et al. |
| 2007/0156034 A1 | 7/2007 | Al-Ali |
| 2007/0208235 A1 | 9/2007 | Besson et al. |
| 2007/0299328 A1 | 12/2007 | Chin et al. |
| 2008/0287757 A1 | 11/2008 | Berson et al. |

FOREIGN PATENT DOCUMENTS

| | | |
|---|---|---|
| GB | 2247838 | 3/1992 |
| JP | 3939782 B2 | 7/2007 |
| JP | 4038280 B2 | 1/2008 |
| WO | WO89/09023 | 10/1989 |
| WO | WO 93/06775 | 4/1993 |
| WO | WO 93/06776 | 4/1993 |
| WO | WO93/06778 | 4/1993 |
| WO | WO 97/29678 | 8/1997 |
| WO | WO 97/47233 | 12/1997 |

* cited by examiner

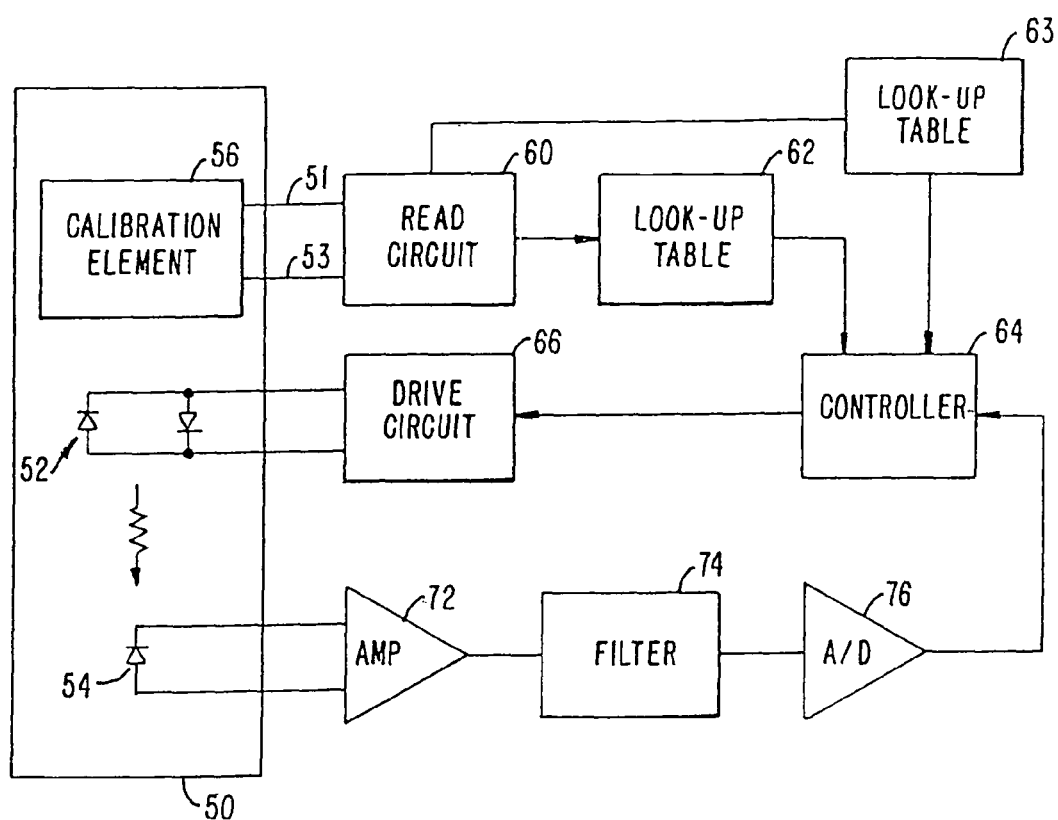

OXIMETER SENSOR WITH DIGITAL MEMORY ENCODING SENSOR DATA

CROSS-REFERENCES TO RELATED APPLICATIONS

This application is a continuation of U.S. patent application Ser. No. 10/440,560, filed May 16, 2003, which is a continuation application of U.S. patent application Ser. No. 09/943,805, filed Aug. 30, 2001, now U.S. Pat. No. 6,591,123, which claims the benefit of U.S. Provisional Application Ser. No. 60/299,616, filed Aug. 31, 2000, all of which are incorporated herein by reference.

BACKGROUND OF THE INVENTION

The present invention relates to oximetry sensors and, in particular, pulse oximetry sensors which include coded information relating to characteristics of the sensor.

Pulse oximetry is typically used to measure various blood flow characteristics including, but not limited to, the blood-oxygen saturation of hemoglobin in arterial blood, the volume of individual blood pulsations supplying the tissue, and the rate of blood pulsations corresponding to each heartbeat of a patient. Measurement of these characteristics has been accomplished by use of a non-invasive sensor which passes light through a portion of the patient's tissue where blood perfuses the tissue, and photoelectrically senses the absorption of light in such tissue. The amount of light absorbed is then used to calculate the amount of blood constituent being measured.

The light passed through the tissue is selected to be of one or more wavelengths that are absorbed by the blood in an amount representative of the amount of the blood constituent present in the blood. The amount of transmitted light passed through the tissue will vary in accordance with the changing amount of blood constituent in the tissue and the related light absorption. For measuring blood oxygen level, such sensors have been provided with light sources and photodetectors that are adapted to operate at two different wavelengths, in accordance with known techniques for measuring blood oxygen saturation.

Nellcor U.S. Pat. No. 5,645,059, the disclosure of which is hereby incorporated herein by reference, teaches coding information in sensor memory used to provide pulse modulated signal, to indicate the type of sensor (finger, nose), the wavelength of a second LED, the number of LEDs, the numerical correction terms to the standard curves, and an identifier of the manufacturer.

BRIEF DESCRIPTION OF THE DRAWINGS

FIG. 1 is a block diagram of a pulse oximeter system in accordance with an exemplary embodiment of the present invention.

DETAILED DESCRIPTION OF THE INVENTION

The present techniques provide a memory chip for use in an oximeter sensor, or an associated adapter or connector circuit. The memory chip allows the storing of different data to provide enhanced capabilities for the oximeter sensor. In addition to providing unique data to store in such a memory, the techniques include unique uses of data stored in such a memory. The data stored in the memory chip includes information relating to use of the oximeter sensor. For example, the memory chip may encode a sensor model identification that can be displayed on a display screen when the sensor is connected to an oximeter monitor. The memory may also encode a range of operating parameters such as light levels over which the sensor can function or a maximum drive current. The operating parameters are read by a controller circuit which uses the data read from the memory chip to control the functioning of the pulse oximetry system.

Part I

FIG. 1 is a block diagram of a pulse oximeter system incorporating a calibration memory element 56 according to the invention. In one embodiment, memory element 56 is a two-lead semiconductor digital memory chip. The calibration element is part of the sensor 50 which also includes red and infrared LEDs 52 as in the prior art, along with a detector 54. If desired, LEDs 52 may be replaced with other light emitting elements such as lasers.

The oximeter includes read circuit 60, drive circuit 66, look-up tables 62 and 63, controller 64, amplifier 72, filter 74, and analog-to-digital converter 76. Read circuit 60 is provided for reading multiple coded values across the two leads 51,53 connected to calibration element 56. One value is provided to a look-up table 62 to determine appropriate wavelength dependent coefficients for the oxygen saturation calculation, as in the prior art. The other value(s) are then provided to another look up table(s) 63 which provides input (e.g., coefficients) to other calculations performed by controller 64. These additional calculations may enhance the performance and/or safety of the system. Controller 64 provides signals to a drive circuit 66, to control the amount of drive current provided to LEDs 52.

As in the prior art, detector 54 is connected through an amplifier 72 and a filter 74 to an A/D converter 76. This forms a feedback path used by controller 64 to adjust the drive current to optimize the intensity range of the signal received. For proper operation the signal must be within the analog range of the circuits employed. The signal should also be well within the range of A/D converter 76 (e.g., one rule that may be applied is to adjust LED drives and amplifier gains so that both red and IR signals fall between 40% and 80% of full scale reading of converter 76). This utilizes correct and independent settings for both the red and infrared LEDs. The current techniques allow for another feedback path which may alter the LED settings based on other sensor characteristics contained in the coding of the calibration element 56, which is discussed in further detail below.

Memory 56 may, for example, be implemented as a random access memory (RAM), a FLASH memory, a programmable read only memory (PROM), an electrically erasable PROM, a similar programmable and/or erasable memory, any kind of erasable memory, a write once memory, or other memory technologies capable of write operations. Various types of data useful to a pulse oximetry system can be stored in memory 56. For example, data indicating a sensor model identification code corresponding to a particular sensor model can be encoded in memory 56. Also, an action can be encoded into memory element 56 indicating an action to be performing by the oximeter monitor in response to reading the sensor model identification code.

For example, an identification code in the form of text indicating the specific model of sensor can be digitally encoded into memory 56 and read by the oximeter monitor when the sensor is connected to the oximeter. An action indicating that the sensor model text is to be displayed by the oximeter monitor on a display screen can also be encoded in memory 56. The identification code can be displayed in human readable form on a display screen connected to the pulse oximeter monitor. The identification code allows the oximeter instrument to display a text string indicating what sensor model is being used, e.g. "Nellcor OXISENSOR I1 D-25," "Adult Digit Sensor," or "Agilent N-25."

Alternately, display text for a plurality of specific models of pulse oximeter sensors can be stored in a lookup table coupled in parallel with lookup tables 62 and 63 in the pulse oximeter monitor. The pulse oximeter monitor reads a sensor code from memory 56 when the sensor 50 is connected to the oximeter. The sensor identification code stored in memory 56 is used to locate display text stored in a lookup table that corresponds to a specific sensor model. The oximeter can display the display text for the specific sensor model on a display screen for viewing.

The present techniques may eliminate the printing of a model name and number on the sensor itself. Even when model names and numbers are printed on a sensor, the text may become illegible after several uses. Displaying text that corresponds to a specific sensor model can be highly useful for users of pulse oximetry sensors. For example, it may be important to identify a sensor model so that instructions relating to a particular sensor model in the manufacturer's handbook can be identified. In addition, it may be desirable to identify a sensor model name or identification number when corresponding with the manufacturer.

Digitally encoded data indicating a sensor model type in memory 56 or in a lookup table may be used to determine whether a sensor model is compatible with a particular pulse oximeter monitor. For example, memory 56 may contain a code indicating a sensor model type that is read by controller 64. Memory 56 can also encode an action indicating that controller 64 is to compare the code from memory 56 with a list of codes in a lookup table (or other oximeter monitor memory device) to determine if the sensor is compatible. If controller 64 successfully matches the code read from the sensor, the display text indicating the sensor model type is displayed on the display screen. If controller 64 does not recognize the code, an error message may be displayed on the display screen indicating that the oximeter monitor does not recognize the sensor, and the oximeter may refuse to operate until the sensor is replaced.

A code can be stored in the sensor memory 56 identifying the sensor manufacturer. An action indicating a use for the code by the oximeter can also be stored in memory 56. The code is read by controller 64 and is used for the purpose indicated by the action. The action may, for example, indicate that the code in memory 56 is to be used to indicate operability with oximeter monitors of other manufacturers. Controller 64 can recognize certain codes as indicating compatible oximeter sensors. If the oximeter monitor does not recognize the code, then controller 64 can display an error message on a display screen indicating that the sensor is not compatible, and/or controller 64 can shut down circuitry in the oximeter monitor that senses signals from the sensor until the sensor is replaced with a compatible sensor.

Other information may also be encoded into memory 56, read by the 17 monitor, and displayed for user reference. For example, language codes or country codes can be stored in memory 56, read, and displayed to the user. The user can select a language or country code so that messages are displayed, such as error messages, in the selected language or a language corresponding to the selected country. Messages may also be encoded into memory 56. For example, safety messages relating to the proper use of the sensor can be encoded in memory 56 and displayed on a display screen in human readable form.

It is often desirable to upgrade the algorithms that are used by the oximeter to determine blood oxygen saturation levels, pulse rates, pulse amplitude, blood pressure, and other patient data as technology progresses and the operating parameters (such as filter coefficients) are refined. Because oximeter sensors are typically much less expensive to replace than oximeter monitor instruments, it is desirable to encode data corresponding to the updated algorithms in the sensors rather than in the oximeter monitors.

One method for performing these updates is by encoding revisions to the algorithms used for calculating the patient parameters in memory within the oximeter monitor, while encoding updated software code or tuning coefficients in sensor memory 56. The updated code or coefficients correspond to updated algorithms that are read by the oximeter monitor so that the updated algorithms can be applied to the standard algorithms preprogrammed into the oximeter. For example, a line of software code in an algorithm used by the oximeter monitor can be replaced by a updated line of code stored in memory 56.

Controller 64 can read the updated code or coefficients from memory 56 and apply the updated algorithms to signals received from detector 54 to determine accurate blood oxygen saturation levels, pulse rates, pulse amplitudes, perfusion data, blood pressure, and other patient data. The updated algorithms can also be used to allow only supported features to be used. In one embodiment, once updated, the new code or coefficients become permanently stored in the oximeter monitor, along with a new algorithm revision number, and are utilized for all future sensor use until later updated.

Encoding a sensor model identification code could also be used to accommodate sensor-specific operating parameters such as LED drive currents or "sensor off" characteristics (as an alternative to programming the value of drive current or "off" characteristics themselves). Under normal operating conditions, photosignals coming from the sensor LEDs generally fall within a certain range. When a sensor is removed from a patient, or falls off on it's own, the photosignal usually changes. This is particularly true for the reusable clip-style sensor, because in their normal disconnected state, the LEDs shine directly onto the photodetector unimpeded by, for example, tissue. By programming a "threshold photocurrent" into memory chip 56, reliable detection of a "sensor is off the patient" condition can be accomplished. In this example, exceeding a certain detected threshold light level is an indication that the sensor is not on a finger or other site.

For certain other sensors, a low light level may be indicative of the sensor being off. An adhesive sensor, for example, lays flat when in it's natural state—little LED light may reach the detector. Encoding an expected range of light levels for the specific model of sensor being used into memory 56 allows enhanced detection of when the sensor is improperly placed or has been removed. When controller 64 senses that the light level output detected by photodetector 54 has fallen below or exceeded the expected range of light levels encoded into memory 56, the oximeter monitor can display an "sensor off" message on a display screen indicating to the medical personnel that the sensor is not in an operable position and that valid data cannot be detected (i.e., a sensor off condition). The oximeter monitor can also emit an alarm signal until the light level detected by photodetector 54 reaches the expected range.

If desired, expected ranges of light levels (or other parameters such as pulse size) that are specific to a particular patient may be encoded and saved into memory 56 by the clinical through the oximeter. The oximeter compares the expected range for the parameters encoded into memory 56 with data received from the photodetector to determine a sensor off condition each time the sensor is used until the range data is overwritten with new data. This is advantageous because light levels, pulse sizes, and other parameters detected by the photodetector can vary significantly from patient to patient.

Existing pulse oximeter sensors determine whether a sensor is off the patient, or not in good contact by using a number of metrics. Those metrics include pulse size, pulse variability, IR/Red correlation, light level variability, pulse shape, and pulse regularity. Not only the light level, but any of these other values could vary depending on the type of sensor, the characteristics of an individual patient, and the location on the body where the sensor is to be applied. Thus, sensor memory 56 could encode information about the expected variation in any of these metrics for the particular sensor type or model or a particular patient, and these metrics may be used in determining if a sensor is off from any combination of these or other metrics as an indication that the sensor is off the patient.

For example, pulses could be typically weaker on the forehead compared to the finger. Memory device 56 of an oximeter sensor designed for use on the forehead of a patient can be encoded with a range of pulse sizes as well as a range of light levels that are expected from that particular oximeter sensor model. If desired, memory 56 can encode a range of numbers based upon light level and pulse size (and other parameters). For example, memory 56 can encode a range of numbers representing the expected range of pulse size times light level received from detector 54 for a specific sensor model.

Controller 64 reads and decodes the pulse size, light level range, and other data encoded in memory 56. Controller 64 then compares the expected pulse size and light level range data with the information received from detector 54. When the pulse size and/or light level data received from detector 54 exceeds or falls below the expected range data encoded in memory 56, the oximeter monitor displays an output message, e.g., a warning of a poor signal, on the display screen indicating that the sensor is not operable or emits an alarm signal. Further details of a Method and Circuit for Indicating Quality and Accuracy of Physiological Measurements are discussed in U.S. patent application Ser. No. 09/545,170, filed Apr. 6, 2000 to Porges, et al., which is incorporated by reference herein in its entirety.

Running LEDs 52 at a high drive current results in more light output from the LEDs, thus improving the signal-to-noise ratio of the blood oxygen saturation signal from detector 54, but comes at a cost of causing additional heat dissipation (i.e., the LEDs run "hotter"). As current flows through the sensor LEDs, the LED emits heat (i.e., the LED power=LED drive current times the voltage drop across the LED). The majority of the energy output by the LEDs is dissipated as heat, and the smaller portion of the energy output by the LEDs is emitted as light. This heat typically causes the temperature of the skin under the sensor to rise by an amount that that depends on the heat dissipation properties of the sensor. Current safety regulations and guidelines limit the temperature of the skin contacting portions of the sensor to remain at or below 41° C. Sensors that do a poor job of directing the heat away from the skin contacting surface, should use a lower LED drive current. Sensors with good thermal management can utilize higher drive currents without risk to the patient.

Accordingly, by encoding the maximum safe LED drive current into the sensor itself, the oximeter instrument can utilize the highest safe drive current for the sensor being used to attain the greatest amount of LED light without risk of injury. The maximum safe drive current allowed to achieve a skin temperature at or below a maximum level can be determined in advance through testing for a given oximeter sensor model. That maximum drive current can be encoded into memory 56 and read by controller 64 when the sensor is connected to the oximeter monitor. Controller 64 then communicates with drive circuit 66 to drive LEDs 52 at or near the maximum drive current value read from memory 56, but to prevent circuit 66 from driving LEDs 52 with a current that exceeds the maximum drive current.

Part II

Embodiments of the present technique include the following:

Sensor Model ID

Encoded text of the specific model of sensor would allow the instrument to display a text string indicating what sensor is being used, e.g. "Nellcor OXISENSOR II D-25" or "Adult Digit Sensor" or "Agilent N-25". Alternately, a sensor code could be stored that points to a lookup table of display text. Encoding sensor model ID could also be used to accommodate sensor-specific operating parameters such as LED drive currents or "sensor off" characteristics (as an alternative to programming the value of drive current or "off" characteristics themselves).

Sensor Model—Specific Information

Coefficients for Taylor's Series Calibration Curves

The sensor may store a general polynomial curve. Other families of polynomials, such as Tchebyschev polynomials, could be used as well. This may also pertain to other calibration information, such as temperature calibration and force transducer calibration. This allows new sensor types (such as a sensor with an offset emitter and detector).

Sensor Adjustment/Re-Application Light Levels

Sensor Off Light Levels

Under normal operating conditions, photosignals coming from the sensor LEDs generally fall within a certain range. When a sensor is removed from a patient, or falls off on its own, the photosignal usually changes. This is particularly true for the reusable clip-style sensor, since in their normal disconnected state, the LEDs shine directly onto the photodetector unimpeded by, for example, tissue. By programming a "threshold photocurrent" into the memory chip, reliable detection of a "sensor is off the patient" condition can be accomplished (in this example, exceeding a certain detected light level is a sure sign the sensor is not on a finger or other opposed site). For certain other sensors, a low light level may be indicative of the sensor being off (an adhesive sensor, for example, lays flat when in its natural state, so little LED light may reach the detector). Encoding an expected range of light levels for the specific model of sensor being used allows enhanced detection of when the sensor is improperly placed or has been removed.

Temperature at which to Switch to STORM Algorithm

The STORM algorithm here refers to the sensors designed to be used where "motion provides the signal", i.e., the cardiac pulse need not be present or discernible in order for the oximeter to provide $SpO_2$ values. Instead, the red and IR waveforms resulting from the motion itself are used for determining the arterial saturation. This feature is possible for tissue beds that are well "arterialized" (a large supply of arterial blood relative to the metabolic needs of the tissue) resulting in a small aterio-venous saturation difference, as well as other signal characteristics that are not germane to this discussion. It has been observed that the necessary degree of arterialization correlates well to being "well perfused" at the tissue site, which itself correlates well to the tissue bed being warm. Thus by monitoring the temperature of the skin at the sensor site, and by knowing a value of temperature (programmed into the memory chip) at which the "motion-is-signal" algorithm can be utilized for the specific sensor design being used, improved reading accuracy through motion can be better accomplished.

Additional Information on Use of Pins

Contact Switch—Sensor Off

Similar to the contact electrodes of the Nellcor FS-14 fetal sensor, an extrinsic probe of skin contact can be used to indicate whether the sensor is in adequate contact to the patient. This extrinsic probe could be accomplished, for example, through an impedance measurement across two electrodes, a force or pressure switch that is sensitive to whether adequate force or pressure is present in the sensor placement, or through other means. Dedicated sensor connector pins, or pin-sharing, could be used to accomplish this additional measure of sensor-patient contact.

Chemical Sensor for EtO Cycles

An electro-chemical or thermal device that senses and stores to memory the number of exposures (zero, once, or potentially more than once or the actual number) to sterilization cycles could be used to capture the history of the sensor. Excessive exposure to sterilization cycles degrades a number of components in the sensor, and can affect its performance. A sensor exceeding a certain number of exposures could cause a display to indicate the sensor needs to be replaced.

Sensor Expiration

This need not be a separate device, but the memory could contain a date after which time the sterilization can no longer be certified as being effective. Sterilization can be sensed and the date recorded automatically by the sensor itself.

Sensor Expiration Date/Sensor Parking: Meter

At the time of manufacture, the expiration date of the sensor may be written into the memory chip. The memory-enabled instrument would then do something with this knowledge (e.g., indicate "expired sensor", or refuse to function if expired). Alternately, the elapsed time of sensor usage could be tracked in the memory chip (written to it by the instrument) and the sensor would "expire" after a memory programmed maximum (greater for reusable sensors than for single-use sensors).

Auto Shut-Off

After sensor expiration, the instrument may refuse to function with this sensor and would indicate that a fresh sensor is needed. Furthermore, the sensor could be disabled by running a high current through it, or by other means.

Warranty Date

Similar to the expiration date, the date of expiration of the sensor warranty could be written into the memory chip (e.g., 2, or 6, or 12, etc. months from the date of 10 manufacture or the date of first use). The instrument would give some indication of this as appropriate.

Patient Specific Information (Written to Sensor from Monitor)

Trending and/or data logging of patient monitoring parameters may be stored in the memory of the memory chip. As the patient and sensor travel from ward-to-ward of the hospital, and consequently plug into different oximeters, the patient-specific data could be displayed as it is contained in the patient's dedicated sensor. Examples of the type of data are given below:

Trending

Low High Sat

The lowest and/or highest $SpO_2$ value during the monitored time, or the lowest/highest values over the past specified monitoring time (e.g., 2 hours, 1 day, etc.)

Duration of Monitoring

How long has the patient been monitored by the pulse oximeter? (elapsed time counter).

Beginning and End of Monitoring

Clock time of when the monitor was turned on and off.

Pre-Set Alarm Limits

The alarm limits used with this patient become written to the memory chip by the instrument. This allows patient-specific alarm values to be set and memorized so that as the patient moves from monitor-to-monitor (the sensor staying with the patient), the appropriate alarm limits need not be reset each time on the new monitor. Instead, this only needs to happen once, or whenever the clinician adjusts alarm limits.

Changeable Key

Data encryption utilizes private and/or public keys to scramble the data written to the memory chip and later decipher the data so that only authorized devices are supported. To further prevent the use with a monitor that is not certified to provide correct results, the sensor manufacturing system could periodically change the private and/or public keys. The change in the key could be communicated to the instrument via the memory chip in encrypted form. The purpose of this feature is to elevate the level of security in the memory system.

Monitor Code Upgrades from Modem or Sensor

Distributing code updates in memory. Whenever an oximeter notes that a code update field is present in the sensor, it would check whether the proposed update had previously been installed, and (if not) whether any indicated prerequisites were present (e.g. a code patch might not function properly in the absence of a previously-circulated patch). If appropriate conditions are met, the code upgrade would be installed. If prerequisites are missing, a message would be displayed to the user, telling him how to obtain the prerequisites (e.g. call Nellcor).

Black Box Encoder (Patient History, Serial Number of Box. Etc.)

Use the memory as a general-purpose carrier of patient data, covering not just oximetry but a lot of other information about the patient.

Optical Efficiency Correction

If it is desirable to know where a particular patient lies in COP space, it is useful to know the inherent brightness of LEDs, sensitivity of detector, and anything else about the particular sensor assembly (e.g. bandage color and alignment) that will affect the amount of light which the sensor receives. Given that information, a measure of the patient's optical transmissivity may be computed for each LED wavelength, which depends almost entirely on the properties of the patient. Signal to noise ratio of the oximeter is probably determined by the size of the detected signal, not by the transmissivity of the patient alone. This could take advantage of DC transmissivity of the tissue to improve the accuracy of pulse oximetry.

Another reason for recording LED and detector parameters in the sensor memory is to provide a basis for later research on the drift of these parameters due to various environmental conditions which the sensor experiences. Parameters of interest include not only LED power and detector sensitivity, but also LED wavelengths, FWHM, and secondary emission level.

Pigment Adjustment Feature

For some types of sensors, the accuracy of the sensor may be different for patients with different skin color. The sensitivity of accuracy to skin color may depend on sensor model. The sensor might contain a sensitivity index, indicating how large an adjustment in readings should be made as a function of skin color. Skin color might be obtained by user entry of the data (e.g. menu selection). Another option would be for the sensor to measure skin color. One way to achieve the latter option would be to provide transmission sensors with auxiliary detector for "reflected" light. In combination with the optical efficiency information noted above, the signal levels reported by the auxiliary detector would sense to what extent the patient's skin was affecting red and IR pathlengths differently, and hence to what extent readings needed to be corrected.

Accelerometer on Chip

This might be used in a scheme in which the memory chip was on the bandage, not in the connector. This combines a MEMS accelerometer with any of several different chips that might usefully be placed in the sensor head, local digitizing chip, preamp chip, memory chip.

Accelerometer data may be used to warn of the presence of motion (in which case special algorithms may be called into play or oximetry may be suspended), or actually to help correct for motion (to the extent to which we can produce algorithms which can predict physio-optic effects of known motion).

Optical Shunt

The amount of optical shunting could be measured for each sensor, or family of sensors. The value would be stored in the sensory memory for the monitor to read and use to adjust the processing coefficients.

Monitor Chip Temperature

The temperature of a red LED, in particular, affects its principal wavelength, which affects calibration. For one class of LEDs, the wavelength shifts by about 0.14 nm/C. The memory chip might contain circuitry capable of monitoring a thermistor or thermocouple, or the memory chip could be mounted in proximity to the LED (e.g. under it), so that it could sense directly the temperature of the LED, and provide a calibration correction accordingly.

Monitor Ambient Temperature

This might be used, e.g., in overseeing the operation of a warmed ear sensor. There is a thermal cutout in the control system of the WES, that causes operation to terminate if the sensor goes over a certain temperature. This is a component for protecting the patient against burns. If the reason for a high sensor temperature is that the environment is warm, it could be quite acceptable to continue oximetry, even though warmer operation would be shut down. In the absence of knowledge about environmental temperature, a high temperature reading might have to be assumed to mean that something was wrong with the sensor, in which case all operation might have to cease. An environmental temperature sensor in the plug could help to tell which rule to apply. Again, the memory chip could record the calibration of whatever device was used for thermometry.

A passive component on the memory chip could be the thermometric sensor, and a resistance or voltage measuring device in the instrument could read out that sensor. Thus, ambient temperature sensing might not require that large changes be made in the memory chip.

Temperature Amplifier/Detector

In illuminating the skin for the purpose of making oxygen saturation measurements, some heat is generated by the LED emitters. Tests have been done to establish the maximum safe current for the LED drive which will assure that the skin temperature stays within a safe value for the worst case sensor/patient conditions. This means that in all cases the sensor will be operated at cooler than the maximum temperature but in most cases well below the maximum temperature.

To establish the optimum signal for the measurement, it is desirable to drive the LEDs with higher current than is imposed by the above limitations. The temperature amplifier/detector would allow the LEDs to be driven to a level that still results in a safe temperature by monitoring the temperature, yet in many cases allow more drive current, and therefore higher signals, which could give better readings.

The inexpensive thermistor devices that could be used in this application are characterized to allow the measurement to be accurate. These characterization values could be stored in the sensor where the thermistor is located. While in operation, the oximeter would be able to read the characterization values from the sensor, measure the resistance of the thermistor, and calculate accurately the temperature of the skin surface where the thermistor is located. This would keep the patient safe from burns and still provide the best signal available.

RCAL Resistance Built into Chip

In legacy oximetry sensors there is a resistor which is selected and installed in the sensor connector, to correspond to the wavelength of the red LED. The wavelength difference from LED to LED has an impact on the calibration of the saturation measurement, if not compensated for. The oximeter will read the value of resistance and adjust its calculation accordingly.

When adding the memory chip, memory compatible oximeters will be able to obtain the necessary calibration coefficients from the memory chip but the legacy instruments will still need a calibration resistor value. If the resistance were built-in to the chip and trimmed or selected at manufacture then only one device would need to be installed in the sensor connector. That would reduce the overall cost, yet keep the sensor compatible with both the legacy instruments and the new memory compatible instruments.

Secondary Emission Measurement

The oximeter is measuring the relative transmission of the red and infrared light through the tissue. LEDs have a characteristic called secondary emission which is indicative of the amount of light, at wavelengths other than the primary wavelength, that is being emitted. This characteristic will change the calibration of the device if not compensated for. It is possible to make an oximeter that will function within calibration if the secondary emission is known and compensated for. If the LED were characterized during manufacture and then the secondary emission values entered into the memory chip, the oximeter would be able to read those values and compensate for them so that the sensor was used properly. This would increase the range of LEDs that could be used for oximetry, reduce cost and provide better calibration across a wider range of LED emitters.

Patient ID (Potentially as Tracking Device, Archiving Patient History, Etc.)

Currently sensors are placed on patients at one hospital site and stay with the patient from hospital site-to-site. It would be helpful to have the patient ID carried along in the sensor so that the record keeping, which occurs at each site, would be able to link the recorded information with the patient. Without patient ID, the tracking has to be done manually. With trend information being stored in the sensor it also would be desirable to have the patient ID included so that as the patient went from location to location, the new location's staff could verify old information and be assured that it correlated with the patient they were receiving.

Encode Contact Resistance (E.g. For Oxicliq)

When making measurements of the resistance that is placed in the sensor for calibration information purposes, one of the factors that can influence that measurement is the contact resistance of the connectors that are between the oximeter and the resistor itself. In order to compensate for connectors that are significant in their impact on the measure, one could encode the contact resistance of the connector and subtract that algorithmically from the measured resistance to get a more accurate measurement of the resistance of the calibration resistor. This would enhance the accuracy with which the resistance measurement is made and, therefore, make the instrument less prone to inaccuracies in saturation calculation and display.

Measure Capacitance to Balance Common Mode Rejection

One of the interfering noise sources that plagues oximetry is that of common mode noise. This can come from the surrounding electrical environment. Other instruments, lighters, drills etc. can produce electrical fields that can couple into the cable between the patient and the oximeter. Once coupled-in, they can make measurements more difficult, less accurate, or not possible, depending on the severity of the noise. To help reduce this common mode noise, differential amplifiers are used for amplifying the signal from the sensor. These amplifiers amplify only the difference between two signal wires. Thus, if the common mode signal is coupled exactly the same into both wires, the amplifier will not amplify it because the same signal is present on both wires.

If the two wires have different coupling to their electrical environment, then they will present different signals, and the difference will be amplified as if it were a signal. One component that influences this coupling is the capacitance of the lines to the outside world. This is affected by the manufacture of the cable, materials, twists in the wire, etc. If one measured the cables during manufacture and then stored that information in the memory chip, it could be read when the oximeter is operating. Once the capacitances for the two wires to the shield are known, the instrument could be provided with a tunable capacitance device that would then balance the two lines again and make the noise coupling to the lines better matched. This would reduce the amount of susceptibility to the external noise that got coupled into the patient cable. Reduced noise results in better measurements or the ability to make measurements at all on some patients.

Fiber-Optic Infrared Wavelength Shift

The relative wavelengths of the red and infrared light that is used to make the measurement in oximetry are important to know so that calibration can be maintained. In traditional LED oximetry, the LED sources are at the skin so that whatever wavelength is emitted is what is sensed by the photodiode that receives the light. The red LED is the only one that we need to characterize for accurate saturation measurements to be realized. The saturation is less sensitive to the IR wavelength as long as it stays fixed in the acceptable range that has been specified for the IR LEDs.

When using plastic fibers for transmission of the light, there is a wavelength dependent absorption caused by the fiber. This has the effect of altering the apparent center wavelength of the IR source, which can affect calibration of the unit. By characterizing the fiber for its shift, one could then provide the proper compensation in the algorithm that calculated the saturation. This would restore the accuracy that would otherwise be lost in fiber transmission of the light.

Inform Monitor of Extra LEDs

There are limitations on the number and type of blood constituents that can be sensed using the two conventional LED wavelengths of the oximeter. The accuracy of the oximetry measurement can also be improved by using different wavelengths at different saturation ranges. An analysis unit could be developed that would utilize either or both of these features. To do this, it would be able to drive additional LEDs.

The additional LEDs could be driven along with the traditional ones or separately. The oximeter (or additional constituent measurement unit) would provide the capability to calculate values for these other wavelengths, and the sensor would provide the additional information to allow the oximeter to make that calculation. These could be stored in the memory.

Active Ambient Light Measurement

One of the problems with oximetry sensors is the interference caused by ambient light in the environment. This can be made worse when a sensor comes loose or when the ambient light is extremely high in value. By characterizing the sensor, one could know what level of ambient light could be expected or tolerated, and give a warning to the user when the level has been exceeded. This would give them the opportunity to adjust the sensor, the light, or both to affect an improvement in the performance of the oximeter.

Active Pressure Adjustment for Modulation Enhancement

The stronger the pulsatile signal, the better the chances are of measuring the saturation accurately. One way to enhance the modulation percentage is to apply pressure in the range of the median pulsatile pressure. If this were implemented, one could use relatively low cost transducers and supply calibration coefficients in the memory to allow accurate pressure readings to be made. The memory could also contain the pressure settings and/or expected modulation enhancement capability to determine effectiveness of the pressure enhancement.

Measure Perfusion

The amount of perfusion affects the amount of modulation, and thus the AC signal. This affects both the percentage of modulation vs. the DC amount, and the absolute size of the modulation. The measured modulation, or other measurement of perfusion, can be stored in memory for trending or setting limits on acceptable perfusion before movement or other adjustment of the sensor is required.

Keep Track of Last Time Sensor Moved or Disconnected

The time of movement or disconnecting of the sensor could be written into the memory. Disconnecting can be detected from the interruption of the signal to the monitor. Moving can be detected by a sensor off detection, and a subsequent sensor on detection. Alternately, aggressive movement could be detected and interpreted as moving of the sensor, or a combination with a sensor off detection could be used.

Identify Private Label Sensors

A code can be stored in the sensor memory identifying the sensor manufacturer. This code can be read and used to indicate operability with monitors of other manufacturers, or to indicate any conversion algorithm that may be needed for a signal from a sensor to be used by a monitor from a different manufacturer. The code can also be used to allow only supported features to be used.

Measure Sensor Wetness

A moisture sensor or impedance sensor can detect the amount of wetness of the sensor. This can be used for different purposes and can be stored in the sensor memory for trending or monitoring. To determine sensor malfunction, the sensor can be disabled if the wetness exceeds a threshold, which could be stored in the sensor memory. Some sensors may not provide for isolation of the patient from the electronics for excessive wetness. The maximum allowable wetness could be stored in the sensor memory.

Sensor Isolation Indicator

The sensor memory could identify that the sensor provides isolation, so wetness is not a concern. Alternately, it could indicate that isolation is not provided by the sensor, or a limited amount of isolation is provided.

Low Power Mode Identifier (Sensor Tells Oximeter to Sleep or Wake Up)

A portable battery-powered monitor can power down when the saturation is at a good level, and the patient is stable. Minimal circuitry in the sensor could be used to do sufficient processing to tell the monitor when to wake up.

Battery to Run Digital Chip

A battery can be included in the sensor for a wireless connection to a monitor. Alternately, a battery could be used to continue to send data when the monitor is powered down.

Motion Generator ("Thumper")

The sensor can include a cuff (which inflates and deflates) or other mechanical mechanism for inducting motion to get a signal or for inducing pulsitile blood flow to improve the signal.

Sensor Force Indicator (E.g., Too Tight)

A transducer can measure the amount of force on the sensor. This can be compared to a maximum value stored in the sensor memory to determine if the sensor is on too tight. The tightness can also be recorded and monitored. For example, a patient could swell, and this could be determined from the trend information and provided as information to a clinician on a display.

Force Transducer Calibration to Get Pressure

A calibration value can be stored in the sensor memory for converting a force measurement into a pressure measurement. A force transducer can then be used to measure pressure.

Number of Wavelengths

The sensor memory can store an indication of the number of wavelengths used in the sensor, and could store the wavelengths themselves.

Drive Information

The sensor memory can store information about when to drive which LEDs. They could all be driven at once, or a subset could be driven, for example.

Display for Additional Wavelengths

The memory can store information about what parameters are to be analyzed and displayed when the extra wavelengths are used. Oxygen saturation may be displayed when 2 wavelengths are used, while additional information could be displayed when an extra wavelength or more are used (Hct, COHb, etc.).

Recycling Times

Each time a sensor is recycled (sterilized and reconstructed), a number in the sensor memory can be incremented. This can be used to prevent operation of the sensor if it has been recycled more than the allowed number of times (e.g., 3 times).

While the present invention has been described herein with reference to particular embodiments thereof, a latitude of modification, various changes and substitutions are intended in the foregoing disclosure, and it will be appreciated that in some instances some features of the invention will be employed without a corresponding use of other features without departing from the scope of the invention as set forth. Therefore, many modifications may be made to adapt a particular situation or material to the teachings of the invention without departing from the essential scope and spirit of the present invention. It is intended that the invention not be limited to the particular embodiments disclosed, but that the invention will include all embodiments and equivalents falling within the scope of the claims.

What is claimed is:

1. A method of oximeter system operation, comprising:
    emitting light from a light emitting element of a sensor;
    detecting the light with a light detecting element of the sensor;
    storing sensor model identification data within a memory of the sensor;
    providing access to the memory to facilitate reading the sensor model identification data with an oximeter monitor;
    storing action data within the memory of the sensor, the action data describing an action to be performed by the oximeter monitor in response to reading the sensor model identification data;
    reading the sensor model identification data and the action data using the oximeter monitor; and
    performing the action in response to reading the sensor model identification data and the action data using the oximeter monitor.

2. The method of claim 1, comprising communicating with a medical facility computer network, the network comprising the oximeter monitor.

3. The method of claim 1, wherein the sensor model identification data is digitally encoded.

4. The method of claim 1, wherein the action comprises displaying text representing the sensor model identification data on a display screen of the oximeter monitor.

5. A method of manufacturing an oximeter system, comprising:
    providing in an oximeter sensor a light emitting element configured to project light into a patient;
    providing in the oximeter sensor a light detector configured to detect the light;
    storing sensor model identification data in a memory of the oximeter sensor;
    providing an access point configured to provide access to the memory to facilitate reading the sensor model identification data with an oximeter monitor;
    storing action data in the memory, the action data describing an action to be performed by the oximeter monitor in response to reading the sensor model identification data; and
    providing a circuit in the oximeter monitor, wherein the circuit is configured to read the sensor model identification data and the action data and to perform the action in response to reading the sensor model identification data and the action data.

6. The method of claim 5, comprising providing a communication mechanism configured to facilitate communication with a medical facility computer network, the network comprising the oximeter monitor.

7. An oximeter system, comprising:
    an oximeter sensor, comprising:
        a light emitting element configured to project light into a patient;
        a light detector configured to detect the light;
        a memory storing sensor model identification data and action data, the action data describing an action to be performed by an oximeter monitor in response to reading the sensor model identification data; and
        an access point configured to provide access to the memory; and
    the oximeter monitor, comprising:
        an output circuit configured to provide signals to the oximeter sensor; and
        a read circuit configured to read the sensor model identification data and action data from the memory of the oximeter sensor via the access point; and a controller circuit configured to perform the action described by the action data in response to reading the sensor model identification data and the action data.

8. The system of claim 7, comprising a communication mechanism configured to facilitate communication with a medical facility computer network, the network comprising the oximeter monitor.

9. The system of claim 7, wherein the action comprises displaying text representing the sensor model identification data on a display screen of the oximeter monitor.

10. An oximeter monitor, comprising:
- a drive circuit configured to provide signals to circuitry of an oximeter sensor that is coupleable to a patient; and
- a circuit configured to receive sensor model identification data and action data from a memory of the oximeter sensor, wherein the action data describes an action to be performed by the oximeter monitor in response to reading the sensor model identification data, and wherein the circuit is configured to perform the action after receiving the sensor model identification data and the action data from the oximeter sensor.

11. A method of oximeter monitor operation, comprising:
- providing signals to circuitry of an oximeter sensor that is coupleable to a patient;
- receiving sensor model identification data and action data from a memory of the oximeter sensor, wherein the action data describes an action to be performed by the oximeter monitor in response to reading the sensor model identification data; and
- performing the action after receiving the sensor model identification data and action data from the oximeter sensor.

* * * * *